(12) United States Patent
Strähle

(10) Patent No.: US 7,643,151 B2
(45) Date of Patent: Jan. 5, 2010

(54) OPTICAL MEASURING DEVICE FOR MEASURING A PLURALITY OF SURFACES OF AN OBJECT TO BE MEASURED

(75) Inventor: Jochen Strähle, Weissach (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 11/662,963

(22) PCT Filed: Jul. 22, 2005

(86) PCT No.: PCT/EP2005/053578

§ 371 (c)(1),
(2), (4) Date: Jan. 14, 2008

(87) PCT Pub. No.: WO2006/032561

PCT Pub. Date: Mar. 30, 2006

(65) Prior Publication Data

US 2008/0259346 A1    Oct. 23, 2008

(30) Foreign Application Priority Data

Sep. 22, 2004   (DE) ................ 10 2004 045 808

(51) Int. Cl.
*G01B 11/02* (2006.01)
(52) U.S. Cl. .................................... 356/497
(58) Field of Classification Search .......... 356/241.1, 356/241.5, 497, 511, 512, 516, 479
See application file for complete search history.

(56) References Cited

U.S. PATENT DOCUMENTS

| | | | | |
|---|---|---|---|---|
| 4,180,322 A | * | 12/1979 | Farcinade | 356/3.06 |
| 4,997,281 A | * | 3/1991 | Stark | 356/328 |
| 6,462,815 B1 | | 10/2002 | Drabarek et al. | |
| 2004/0075842 A1 | | 4/2004 | Dunn et al. | |

FOREIGN PATENT DOCUMENTS

DE     198 19 762     11/1999

(Continued)

OTHER PUBLICATIONS

T. Dresel, G. Häusler, H. Venzke; "Three-Dimensional Sensing of Rough Surfaces by Coherence Radar"; Appl. Opt. 31 (7), p. 919-925, 1992.

*Primary Examiner*—Tarifur Chowdhury
*Assistant Examiner*—Jonathon D. Cook
(74) *Attorney, Agent, or Firm*—Kenyon & Kenyon LLP

(57) ABSTRACT

An optical measuring device for measuring a plurality of surfaces of an object to be measured using a system of optical elements. For example, the first surface to be measured can be the inner wall of a narrow guide bore, while the second surface to be measured is formed by a valve-seat section that is conical and positioned at one end of the guide bore. As optical elements of measuring device, at least one beam splitter and one lens system are disposed in such a way that a first portion of the light beams incident on the beam splitter is directed perpendicularly onto the first surface of the object to be measured, and a second portion of the light beams incident on the beam splitter strikes the lens system downstream of the beam splitter and is directed via the lens system perpendicularly onto the second surface.

18 Claims, 4 Drawing Sheets

FOREIGN PATENT DOCUMENTS

| | | |
|---|---|---|
| DE | 10131778 A1 * | 1/2003 |
| DE | 101 31 778 | 5/2003 |
| DE | 102 04 136 | 8/2003 |
| DE | 103 01 607 | 8/2004 |
| DE | 103 25 443.9 | 12/2004 |

* cited by examiner

OPTICAL MEASURING DEVICE FOR MEASURING A PLURALITY OF SURFACES OF AN OBJECT TO BE MEASURED

FIELD OF THE INVENTION

The present invention relates to an optical measuring device for measuring a plurality of surfaces of an object to be measured using a system of optical elements. The present invention further relates to a utilization of the optical measuring device as an objective for the object to be measured.

BACKGROUND INFORMATION

Interferometric systems are suited, inter alia, for the contact-free examination of surfaces of various objects to be measured. To detect the surface contour of an object to be examined, an object beam from a light source of the interferometer strikes the surface at the area to be measured. The object beam reflected by the surface is supplied to a detector of the interferometer and, together with a reference beam, forms an interference pattern, from which it is possible to derive the difference in path length of the two beams. This measured difference in the path length of the two beams corresponds to the change in the surface topography.

Particularly with a white-light interferometer, in which the light source emits a short-coherent radiation, it is also possible to scan the object to be measured with the aid of depth scanning. As explained, for instance, in the non-prepublished German Patent Application No. DE 103 25 443.9, in that case, the short-coherent radiation is split by a beam splitter into an object beam and a reference beam. The object surface to be measured is imaged via an objective onto an image recorder, e.g., a CCD camera (charge-coupled device camera), and superposed by the reference wave formed by the reference beam. The depth scanning may be implemented by moving a reference mirror reflecting the reference beam, or moving the object relative to the measuring device. When the object is moved, the image plane of the object and the reference plane are in the same plane. During depth scanning, the object remains fixed in the field of view of the CCD camera, and the object is only moved along the depth axis relative to the reference plane. In this manner, measurements of industrial surfaces may be conducted with a depth resolution in the range of a few nanometers. Technical fundamentals concerning this measuring method are also found in the "Three-Dimensional Sensing of Rough Surfaces by Coherence Radar"(T. Dresel, G. Häusler, H. Venzke, Appl. Opt. 31 (7), p. 919-925, 1992).

If, in this context, the measurement-object surface to be measured is not a uniform, level plane, then a special-purpose objective is necessary for measuring the object to be measured, for in each measuring procedure, care must be taken that, during scanning, the beams strike as perpendicularly as possible on the surfaces to be measured. For example, German Patent Application No. DE 101 31 778 describes a system of optical elements by which it is also possible to measure curved surfaces. Thus, for example, FIG. 1c from the cited document, reproduced herein as FIG. 5, shows how surfaces to be measured which are not easily accessible such as the inner surface of a cylinder or a bore can also be measured using the panoramic optics presented there. With the aid of a deviating prism in the panoramic optics, the beams are directed perpendicularly onto the inner surface of the bore. In a further exemplary embodiment, as illustrated n FIG. 1d of the cited document, reproduced herein as FIG. 6,the panoramic optics may be designed for an inner conical surface in a transition region of the bore. With the aid of the special optics, the parallel beams striking the optics are converted on the object side into beams which are disposed perpendicularly to the conical surface, i.e., the beams are fanned out. In practice, however, it is advantageous if both surfaces, thus the inner surface of a bore and the inner conical surface produced by a further narrowing of the bore, can be measured simultaneously. Such demands arise, for instance, when the position of a guide bore leading to a conical valve seat is measured. According to the related art, two or more panoramic optics may be arranged and designed in such a way that, in addition to being able to generate a flattened image from one surface area, it is possible to generate a flattened image from at least one further surface area at the same time. Likewise, at least one further reference plane may then be disposed in the reference light path according to the number of further surface areas for generating different optical path lengths. It is thus possible to measure the position of the guide bore leading to a spatially separated valve seat.

Thus, it is not possible to measure the two surfaces using only one objective. A simple combination of the two exemplary embodiments having a deflection mirror (FIG. 5) and having a beam-fanning optics (FIG. 6) from the related art would not be successful, since the beams would either cover only the inner surface of the bore or only the inner conical surface, depending on the order of the installation of the two optical elements.

SUMMARY OF THE INVENTION

Compared to the related art, the optical measuring device of the present invention has the advantage that it makes it possible to measure a plurality of hard-to-access surfaces of an object to be measured. Particularly advantageous, the different surfaces to be measured, such as conical surfaces and inner surfaces of a bore, may be measured quickly and without altering the measuring device. The optical measuring device may also be used as a special-purpose objective for the object to be measured in a measurement set-up of an interferometer, known per se, or in an autofocus sensor.

DETAILED DESCRIPTION

Figure 1:
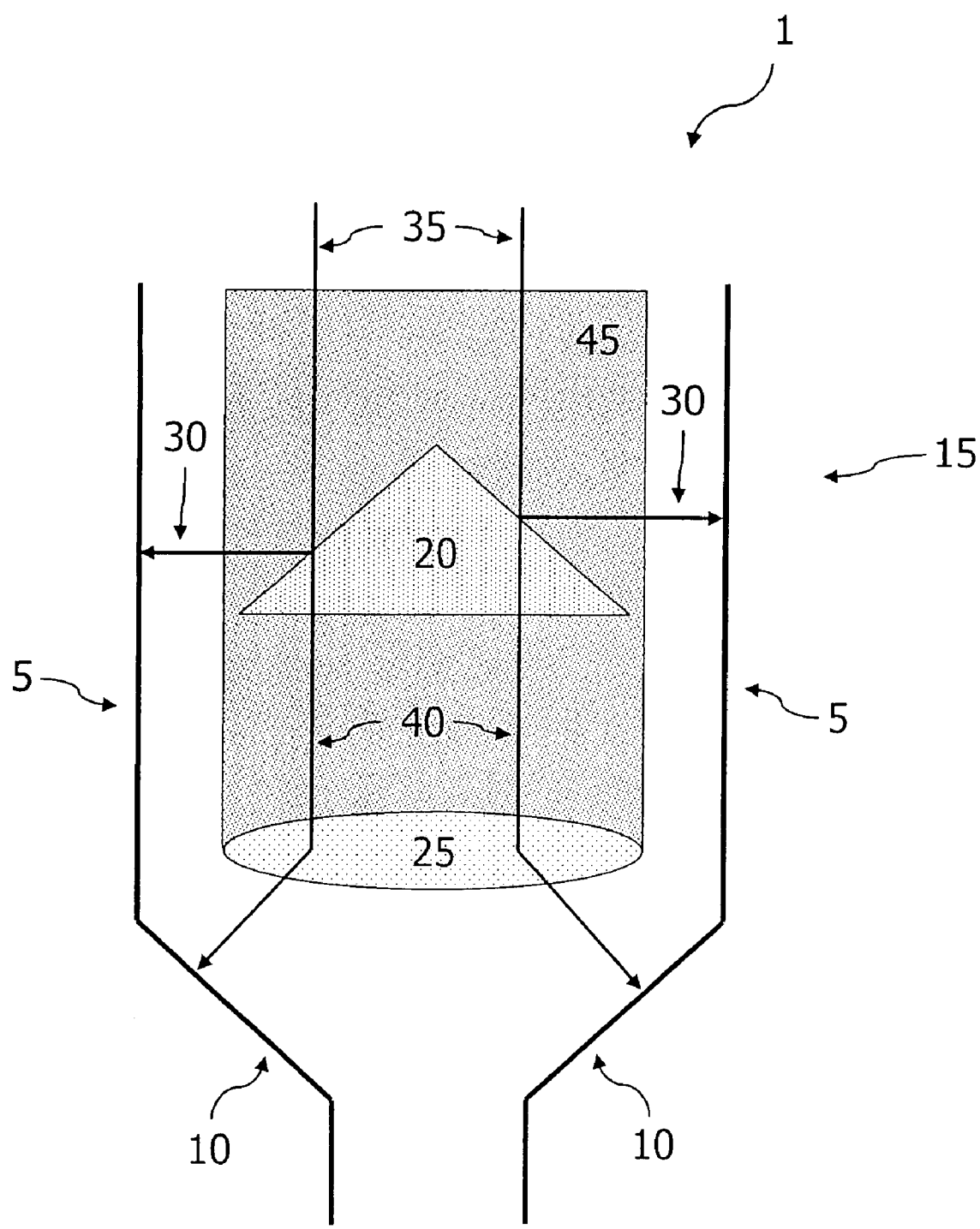
FIG. 1 shows a first configuration of a system of optical elements in the measuring device.

FIG. 1 shows a first configuration of measuring device 1 according to the present invention, having a system of optical elements. This example shows a guide bore as object to be measured 15, whose diameter changes through a transition region from a constantly higher value to a constantly lower value. The transition region itself exhibits a continuous narrowing of the bore, thereby forming the surface shape of a section of an inner conical surface. Such a geometry corresponds to that of a guide bore having a conical, i.e., cone-shaped valve seat. The inner wall corresponds to a first surface 5, and the conical valve seat corresponds to a second surface 10 of object to be measured 15. To measure the inner wall of the guide bore and the conical valve seat, according to the present invention, at least one beam splitter 20 and one lens system 25 are provided as optical elements, a first portion 30 of light beams 35 incident on beam splitter 20 being directed perpendicularly onto first surface 5 of object to be measured 15, and a second portion 40 of light beams 35 incident on beam splitter 20 striking lens system 25, situated downstream of beam splitter 20, and being directed via lens system 25 perpendicularly onto second surface 10. Beam splitter 20 advantageously turns first portion 30 of light beams 35, incident on beam splitter 20, through a right angle with respect to the direction of incidence. Second portion 40 of light beams 35 incident on beam splitter 20 is directed without any deflection onto lens system 25.

To permit the splitting of light beams 35 into first portion 30 and second portion 40, beam splitter 20 is semi-transparent to light, i.e., first portion 30 of light beams 35 is reflected at beam splitter 20, while second portion 40 penetrates beam splitter 20. In FIG. 1, beam splitter 20 is a prism semi-transparent to light. Beam splitter 20, here the prism, and/or lens system 25 also has/have an axisymmetrical shape, corresponding to the axisymmetrical shape of object to be measured 15. Lens system 25 fans out second portion 40 of beams 35 in a cone shape, so that it strikes the conical valve seat perpendicularly at each location. Both first portion 30 and second portion 40 of light beams 35 split by beam splitter 20 are reflected back at first surface 5 or second surface 10 of object to be measured 15 to the light-beam-incident side of measuring device 1 facing away from the object.

The optical elements are usually disposed in a tube 45, especially in an exit region of tube 45. At the locations at which first portion 30 or second portion 40 of light beams 35 emerge from the tube or enter the tube again after the respective reflection, the tube is made of an optically transparent material, or the material is eliminated completely to form a cut-out. For reasons of clarity, the optically transparent material or the cut-out are not shown in the Figures.

Figure 2:
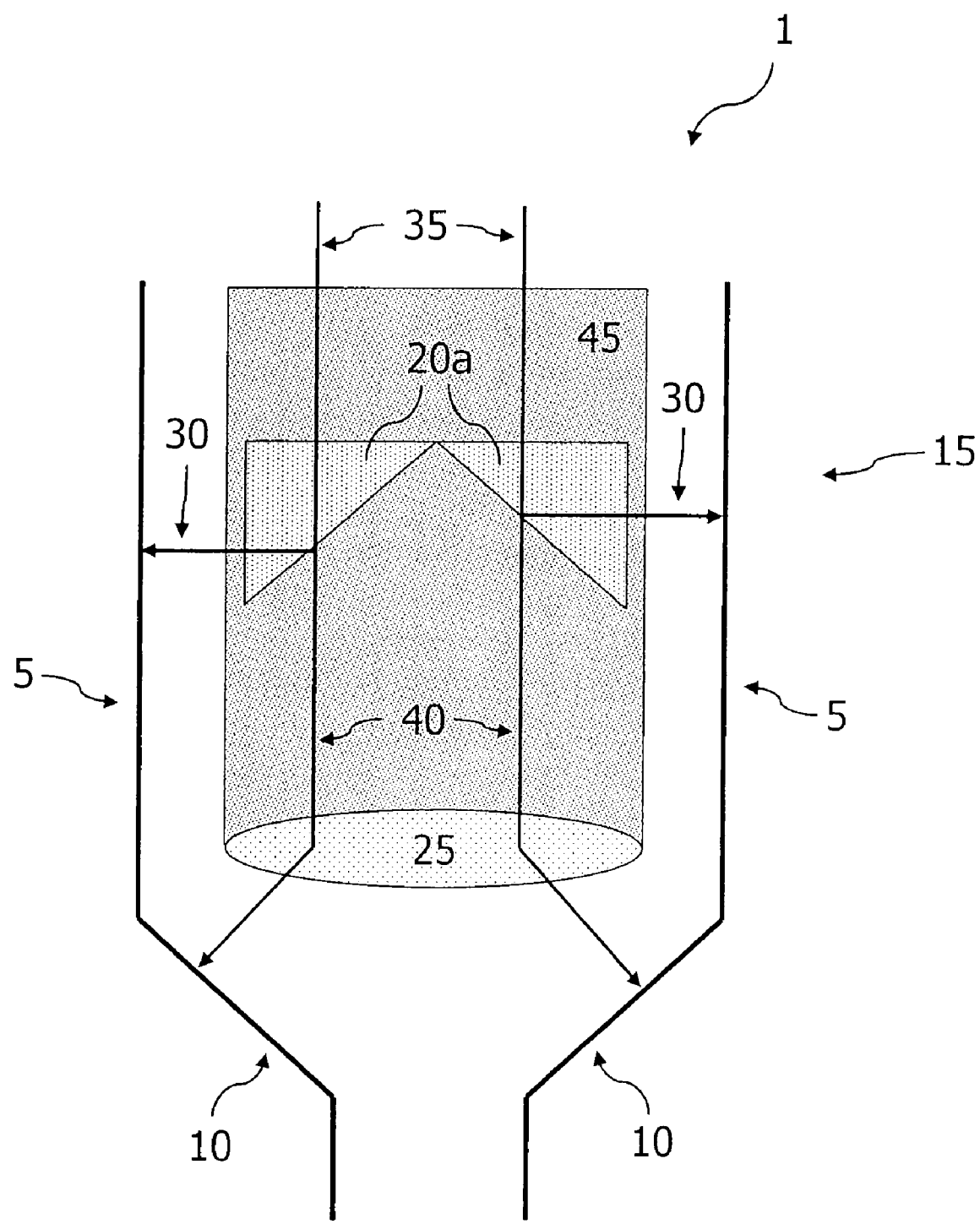
FIG. 2 shows a second configuration of a system of optical elements in the measuring device.

FIG. 2 shows a second specific embodiment of measuring device 1. It differs from the first exemplary embodiment in that beam splitter 20a is formed by a hollow cone, i.e., beam splitter 20a is a disk semi-transparent to light, which has a cut-out in the form of an axisymmetrical prism.

Figure 3:
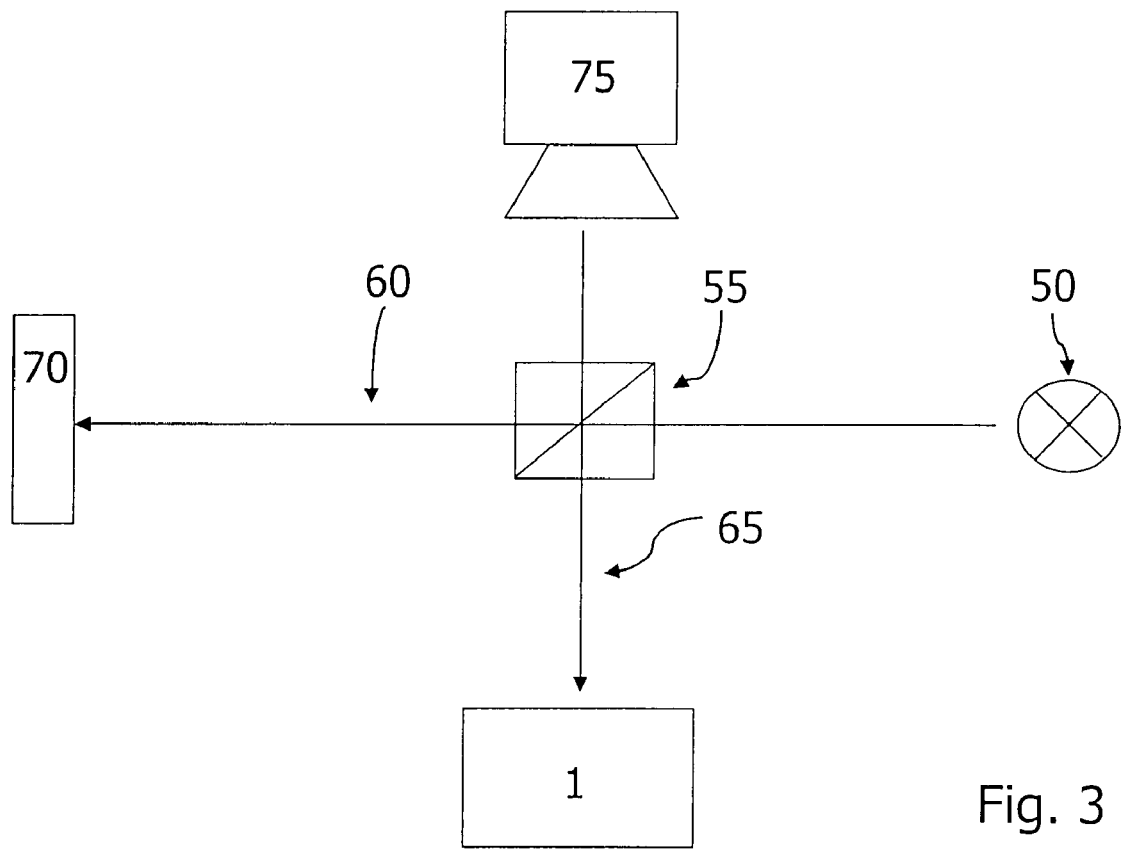
FIG. 3 shows an interferometric measurement set-up having the measuring device of the present invention as a special-purpose objective.

Measuring device 1 is suited for utilization as a special-purpose objective for an object to be measured 15 in a measurement set-up of an interferometer, known per se, especially a white-light interferometer. A measurement set-up according to Michelson is shown in FIG. 3 and its measuring principle is familiar: In white-light interferometry (short-coherence interferometry), a light source 50 outputs a short-coherent radiation. The light is split by a beam splitter 55 of the interferometer into a reference beam 60 and an object beam 65. Beam splitter 55 of the interferometer is to be differentiated from beam splitter 20, 20a of measuring device 1. Reference beam 60 is further reflected by a reference mirror 70 situated in the reference light path and arrives again via beam splitter 55 at an image recorder 75, advantageously a CCD or CMOS camera (complementary metal oxide semiconductor camera). There, the light waves of reference beams 60 are superimposed with the light waves of object beams 65, which on their part were directed via the special-purpose objective according to the present invention situated in the object light path, onto first and second surfaces 5, 10 of object to be measured 15 and were reflected. As already explained, according to the present invention, object beams 65, i.e., light beams 35 incident on beam splitter 20, 20a of measuring device 1, are split into a first portion 30 and second portion 40 to permit the measurement of two surfaces. Naturally, use of measuring device 1 as a special-purpose objective in a measurement set-up of an autofocus sensor or a laser-, heterodyne- or other type of interferometer is also possible.

During the measurement, a relative movement of measuring device 1 with respect to object to be measured 15 or vice versa is preferably to be avoided. Therefore, measuring device 1 is especially suitable as a special-purpose objective of an interferometer having an intermediate image. Such interferometers having the possibility for generating the intermediate image are known from the related art.

Incidentally, it is important when measuring first surface 5 and second surface 10 of object to be measured 15 that the two surfaces 5, 10 are not in the focus of image recorder 75 simultaneously. The beams reflected by the two surfaces 5, 10 and transferred into image recorder 75 would then be superimposed to form a joint interference image and thus invalidate the measurement values. Therefore, initially first surface 5 is scanned until it emerges from the interference region, before second surface 10 enters the interference region and is also scanned. Naturally, surfaces 5, 10 may also be scanned in reverse order. To avoid overlapping of first portion 30 and second portion 40 of light beams 35 in image recorder 75, care must be taken in the arrangement of the optical elements of measuring device 1 with respect to the coherence length of light beams 35. Understood by a coherence length of a wave train is the connection length, necessary for interference, for an overlap. Therefore, taking into account the overlap condition just described, the optical elements of measuring device 1 are arranged in such a way that the optical paths of first portion 30 and second portion 40 of incident light beams 35 differ at least in the order of magnitude of a coherence length of light beams 35. A typical value range of a coherence length when working with a white-light interferometer is approximately 2 to 14 μm, while in the case of a heterodyne interferometer with wavelengths of approximately 1570 μm employed, a coherence length of approximately 80 μm results.

Alternatively or in addition to the arrangement of measuring device 1 having different path lengths for first portion 30 and second portion 40 of light beams 35, an interfering overlap of the two beam components 30, 40 in image recorder 75 may be prevented, in that beam splitter 20, 20a is electrically or magnetically controllable in order to selectively vary its transmission and reflection properties. Thus, the light path of first portion 30 or second portion 40 of light beams 35 is blocked for a short period.

Figure 4:
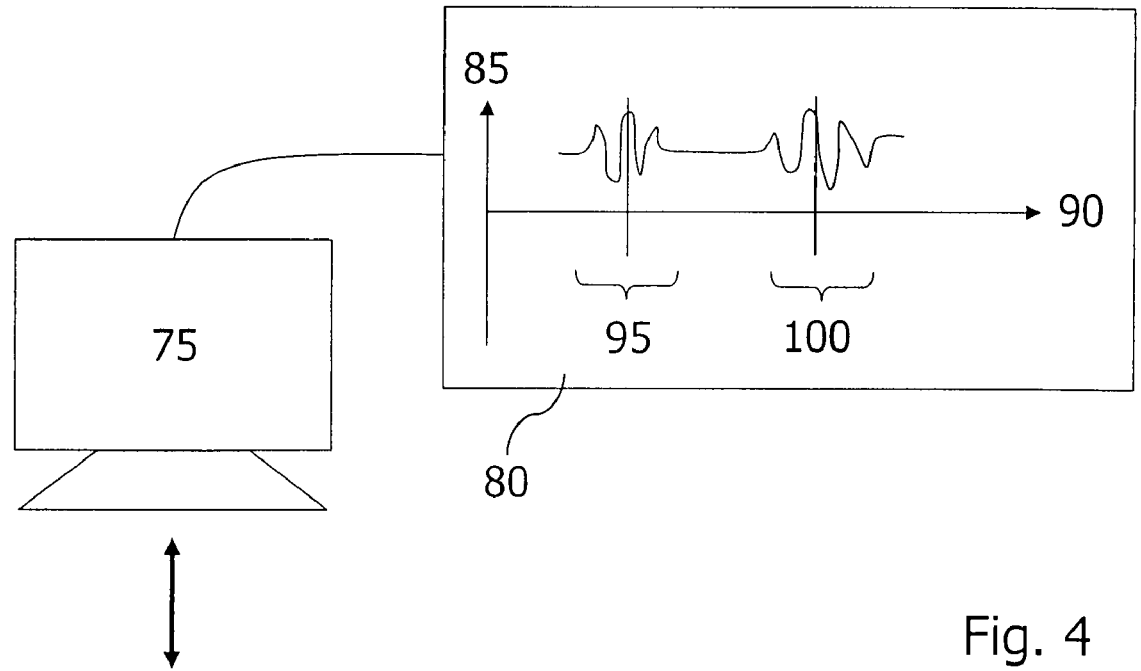
FIG. 4 shows an image recorder having evaluation software for a double correlogram.
Figure 5:
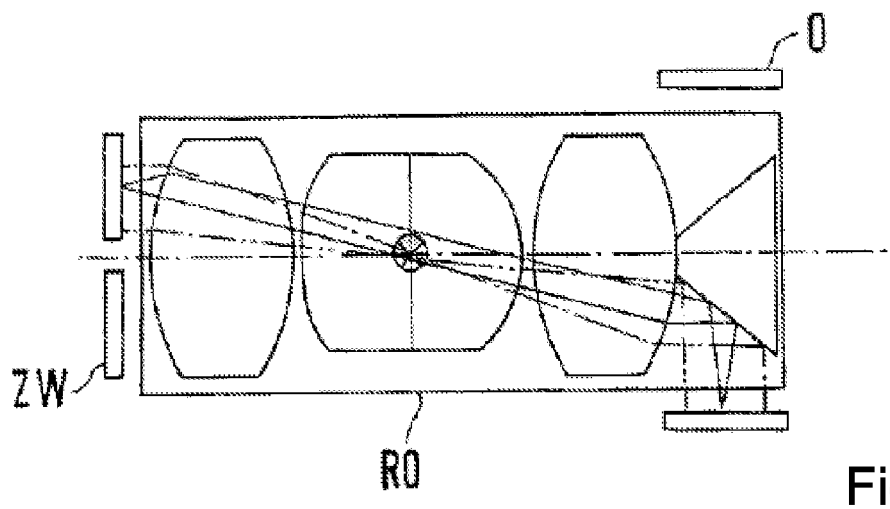
FIG. 5 shows an example embodiment having a deflection mirror according to the related art.
Figure 6:
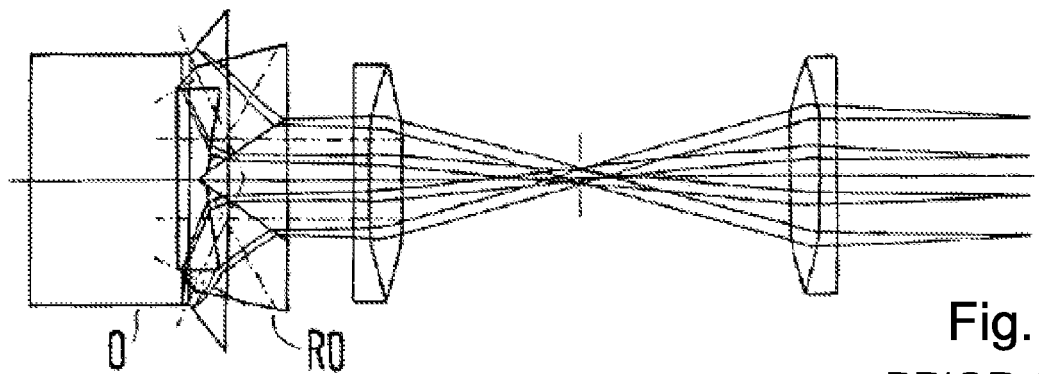
FIG. 6 shows an example embodiment having a beam-fanning optics according to the related art.

In this connection, it is advantageous to use an image recorder 75 having evaluation software for a double correlogram 80. Since, according to the present invention, optical measuring device 1 permits the measurement of a plurality of surfaces 5, 10 of an object to be measured 15, image recorder 75 must accordingly evaluate the beam components, reflected by different surfaces, separately. As FIG. 4 shows clearly, the interference pattern generated in image recorder 75 is evaluated separately according to its intensity 85 and position 90, so that two successive correlograms 95, 100 are formed with the aid of the evaluation software.

In summary, splitting light beams 35 into a first portion 30 and second portion 40 in measuring device 1 permits the measurement of a plurality of surfaces 5, 10 of an object to be measured 15. In particular, the arrangement of the optical elements allows the measurement of an inner surface of a cylinder and that of a cone-shaped surface using only one measuring device 1.

What is claimed is:

1. An optical measuring device for measuring a first surface and a second surface of an object to be measured using a system of optical elements, comprising:
    at least one beam splitter; and
    a lens system;
    wherein the beam splitter and the lens system are situated such that:
        a first portion of light beams incident on the beam splitter is directed perpendicularly onto the first surface of the object to be measured, and a second portion of the light beams incident on the beam splitter strikes the lens system downstream of the beam splitter and is directed via the lens system perpendicularly onto the second surface; and
        optical paths of the first portion and of the second portion of the incident light beams differ at least in an order of magnitude of a coherence length of the light beams.

2. The optical measuring device according to claim 1, wherein the beam splitter at least one of(a) turns the first portion of the light beams, incident on the beam splitter, through a right angle with respect to a direction of incidence and (b) directs the second portion of the light beams, incident on the beam splitter, without any deflection onto the lens system.

3. The optical measuring device according to claim 1, wherein a transmission and a reflection of the beam splitter are variable by one of electrical and magnetic control.

4. The optical measuring device according to claim 1, wherein the beam splitter includes one of a prism and a hollow cone.

5. The optical measuring device according to claim1, wherein at least one of the beam splitter and the lens system has an axisymmetrical form.

6. The optical measuring device according to claim 1, wherein the lens system fans out the second portion of the incident light beams in a cone shape.

7. The optical measuring device according to claim 1, wherein the beam splitter and the lens system are situated in an exit region of a tube.

8. The optical measuring device according to claim 1, wherein the measuring device is used as a special-purpose objective for the object to be measured in a measurement set-up of one of an autofocus sensor and an interferometer.

9. The optical measuring device according to claim 8, wherein the interferometer is one of a laser interferometer, a heterodyne interferometer and a white-light interferometer.

10. The optical measuring device according to claim 8, wherein the measuring device is used together with an image recorder having evaluation software for a double correlogram.

11. An optical measuring device for measuring a first surface and a second surface of an object to be measured using a system of optical elements, comprising:
    at least one beam splitter; and
    a lens system;
    wherein:
        the beam splitter and the lens system are situated such that a first portion of light beams incident on the beam splitter is directed perpendicularly onto the first surface of the object to be measured, and a second portion of the light beams incident on the beam splitter strikes the lens system downstream of the beam splitter and is directed via the lens system perpendicularly onto the second surface; and
        the measuring device is used:
            as a special-purpose objective for the object to be measured in a measurement set-up of one of an autofocus sensor and an interferometer; and
            together with an image recorder having evaluation software for a double correlogram.

12. The optical measuring device according to claim 11, wherein the beam splitter at least one of (a) turns the first portion of the light beams, incident on the beam splitter, through a right angle with respect to a direction of incidence and (b) directs the second portion of the light beams, incident on the beam splitter, without any deflection onto the lens system.

13. The optical measuring device according to claim 11, wherein a transmission and a reflection of the beam splitter are variable by one of electrical and magnetic control.

14. The optical measuring device according to claim 11, wherein the beam splitter includes one of a prism and a hollow cone.

15. The optical measuring device according to claim 11, wherein at least one of the beam splitter and the lens system has an axisymmetrical form.

16. The optical measuring device according to claim 11, wherein the lens system fans out the second portion of the incident light beams in a cone shape.

17. The optical measuring device according to claim 11, wherein the beam splitter and the lens system are situated in an exit region of a tube.

18. The optical measuring device according to claim 11, wherein the interferometer is one of a laser interferometer, a heterodyne interferometer and a white-light interferometer.

* * * * *